US011564857B2

(12) United States Patent
Bilodeau et al.

(10) Patent No.: US 11,564,857 B2
(45) Date of Patent: Jan. 31, 2023

(54) LOAD BEARING ASSISTANCE APPARATUS FOR LOWER EXTREMITY ORTHOTIC OR PROSTHETIC DEVICES

(71) Applicant: B-TEMIA INC., St-Augustin-de-Desmaures (CA)

(72) Inventors: Katia Bilodeau, Québec (CA); Benoit Gilbert, Lac Beauport (CA); Stéphane Bédard, Lévis (CA)

(73) Assignee: B-Temia iNC., St-Augustin-de-Desmaures (CA)

( * ) Notice: Subject to any disclaimer, the term of this patent is extended or adjusted under 35 U.S.C. 154(b) by 0 days.

(21) Appl. No.: 16/072,871

(22) PCT Filed: Jan. 25, 2017

(86) PCT No.: PCT/CA2017/000017
§ 371 (c)(1),
(2) Date: Jul. 25, 2018

(87) PCT Pub. No.: WO2017/127915
PCT Pub. Date: Aug. 3, 2017

(65) Prior Publication Data
US 2018/0369056 A1 Dec. 27, 2018

Related U.S. Application Data

(60) Provisional application No. 62/286,903, filed on Jan. 25, 2016.

(51) Int. Cl.
*A61H 3/00* (2006.01)
*A61F 2/66* (2006.01)
*A61F 5/01* (2006.01)

(52) U.S. Cl.
CPC .............. *A61H 3/00* (2013.01); *A61F 2/66* (2013.01); *A61F 5/0111* (2013.01);
(Continued)

(58) Field of Classification Search
CPC ........ B25J 9/0006; B25J 9/104; B25J 9/1694; A61H 3/00; A61H 2201/0192;
(Continued)

(56) References Cited

U.S. PATENT DOCUMENTS 3,036,389 A * 5/1962 Wesch ...................... A43B 5/18
36/7.8
4,912,859 A * 4/1990 Ritts ..................... A43B 13/184
36/7.8
(Continued)

FOREIGN PATENT DOCUMENTS

EP 0103041 A1 * 3/1984 ............. A63B 25/10

OTHER PUBLICATIONS

English translation for EP 0103041, machine translated by SEARCH Clarivate Analytics, translated on Sep. 24, 2022.*

*Primary Examiner* — Tu A Vo
(74) *Attorney, Agent, or Firm* — Praxis

(57) ABSTRACT

A load bearing assistance apparatus for transferring load from a lower extremity orthotic or prosthetic device to the ground. The load bearing assistance apparatus includes a lateral and a medial spring-loaded members and a linking mechanism for connecting the load bearing assistance apparatus to the lower extremity orthotic or prosthetic device. The linking mechanism also connects the lateral and medial spring-loaded members in a spaced apart configuration so as to position them adjacent the lateral and medial portions, respectively, of the foot of the user of the lower extremity orthotic or prosthetic device and such that a portion of the lateral and medial spring-loaded members enters in contact with the ground during locomotion.

4 Claims, 6 Drawing Sheets

(52) U.S. Cl.
CPC .... *A61F 5/0127* (2013.01); *A61F 2002/6664* (2013.01); *A61F 2002/6671* (2013.01); *A61F 2002/6685* (2013.01); *A61F 2005/0179* (2013.01); *A61H 2201/0192* (2013.01); *A61H 2201/164* (2013.01); *A61H 2201/165* (2013.01)

(58) Field of Classification Search
CPC ........ A61H 2201/164; A61H 2201/165; A61H 1/00; A61H 1/0262; A61H 1/0266; A61F 2/66; A61F 5/0111; A61F 5/0127; A61F 2002/6664; A61F 2002/6671; A61F 2002/6685; A61F 2005/0179
See application file for complete search history.

(56) References Cited

U.S. PATENT DOCUMENTS

| | | | | |
|---|---|---|---|---|
| 5,282,325 | A * | 2/1994 | Beyl | A43B 21/30 36/38 |
| 6,684,531 | B2 * | 2/2004 | Rennex | A43B 13/184 36/31 |
| 2002/0083616 | A1 * | 7/2002 | Hajianpour | A43B 13/182 36/7.8 |
| 2003/0188455 | A1 * | 10/2003 | Weaver | A43B 3/0063 36/27 |
| 2004/0040180 | A1 * | 3/2004 | Rennex | A43B 13/184 36/35 R |
| 2005/0262725 | A1 * | 12/2005 | Rennex | A43B 13/181 36/7.8 |
| 2010/0210983 | A1 * | 8/2010 | Baker | A43B 13/12 601/152 |
| 2011/0010964 | A1 * | 1/2011 | Hardy | A43B 13/182 36/103 |
| 2011/0319801 | A1 * | 12/2011 | Ital | A61F 5/0102 602/23 |
| 2013/0119622 | A1 * | 5/2013 | Othman | A63C 17/12 280/11.115 |
| 2013/0197407 | A1 * | 8/2013 | Flythe, Jr. | A61H 1/0262 601/34 |
| 2014/0000125 | A1 * | 1/2014 | Butler | A43B 7/28 36/43 |
| 2014/0298679 | A1 * | 10/2014 | Brun del Re | A43B 13/184 36/27 |

* cited by examiner

LOAD BEARING ASSISTANCE APPARATUS FOR LOWER EXTREMITY ORTHOTIC OR PROSTHETIC DEVICES

CROSS-REFERENCE TO RELATED APPLICATIONS

This application claims the benefits of U.S. provisional patent application No. 62/286,903 filed on Jan. 25, 2016, which is herein incorporated by reference.

TECHNICAL FIELD

The present disclosure relates to a load bearing assistance apparatus for lower extremity orthotic or prosthetic devices. More specifically, the present disclosure relates to a load bearing assistance apparatus for transferring load from a lower extremity orthotic or prosthetic device to the ground.

BACKGROUND

Soldiers and other users of lower extremity orthotic devices must support the weight of their gear as well as the weight of the devices.

A common solution is to provide lower extremity orthotic devices with a ground contact portion positioned underneath the foot of the wearer, for example by a metal sole placed under the foot. However, such solution has for effect to completely separate the wearer from his environment and thus reduces the stability and agility of the wearer.

Accordingly, there is a need for a load bearing assistance apparatus for lower extremity orthotic or prosthetic devices that does not completely separates the wearer from his environment.

SUMMARY

The present disclosure provides a load bearing assistance apparatus for transferring load from a lower extremity orthotic or prosthetic device to the ground, comprising:
  a lateral and a medial spring-loaded members; and
  a linking mechanism for connecting the load bearing assistance apparatus to the lower extremity orthotic or prosthetic device and connecting the lateral and medial spring-loaded members in a spaced apart configuration so as to position the lateral and medial spring-loaded members adjacent a lateral and a medial portions, respectively, of a foot of a user of the lower extremity orthotic or prosthetic device and such as a portion of the lateral and medial spring-loaded members enters in contact with the ground during locomotion;
  wherein in use the lateral and medial spring-loaded members transfer the load from the lower extremity orthotic or prosthetic device to the ground.

The present disclosure also provides a load bearing assistance apparatus as disclosed above, wherein each of the lateral and medial spring-loaded members is composed of a first and second convex elements connected at respective ends, a side-wise C-like and a slightly downwardly curved longitudinal elements or two opposed side-wise C-like elements connected so as to form a S-like shape.

The present disclosure further provides a load bearing assistance apparatus as disclosed above, further comprising a spring-loaded members tension adjustment mechanism, for example a spring-loaded members height adjustment mechanism.

BRIEF DESCRIPTION OF THE FIGURES

Embodiments of the disclosure will be described by way of examples only with reference to the accompanying drawings, in which.

Similar references used in different Figures denote similar components.

DETAILED DESCRIPTION

Generally stated, the non-limitative illustrative embodiments of the present disclosure provide a load bearing assistance apparatus for lower extremity orthotic or prosthetic devices that transfers all or part of the load from a lower extremity orthotic or prosthetic device to the ground while allowing the user to maintain contact with his environment.

Figure 1:
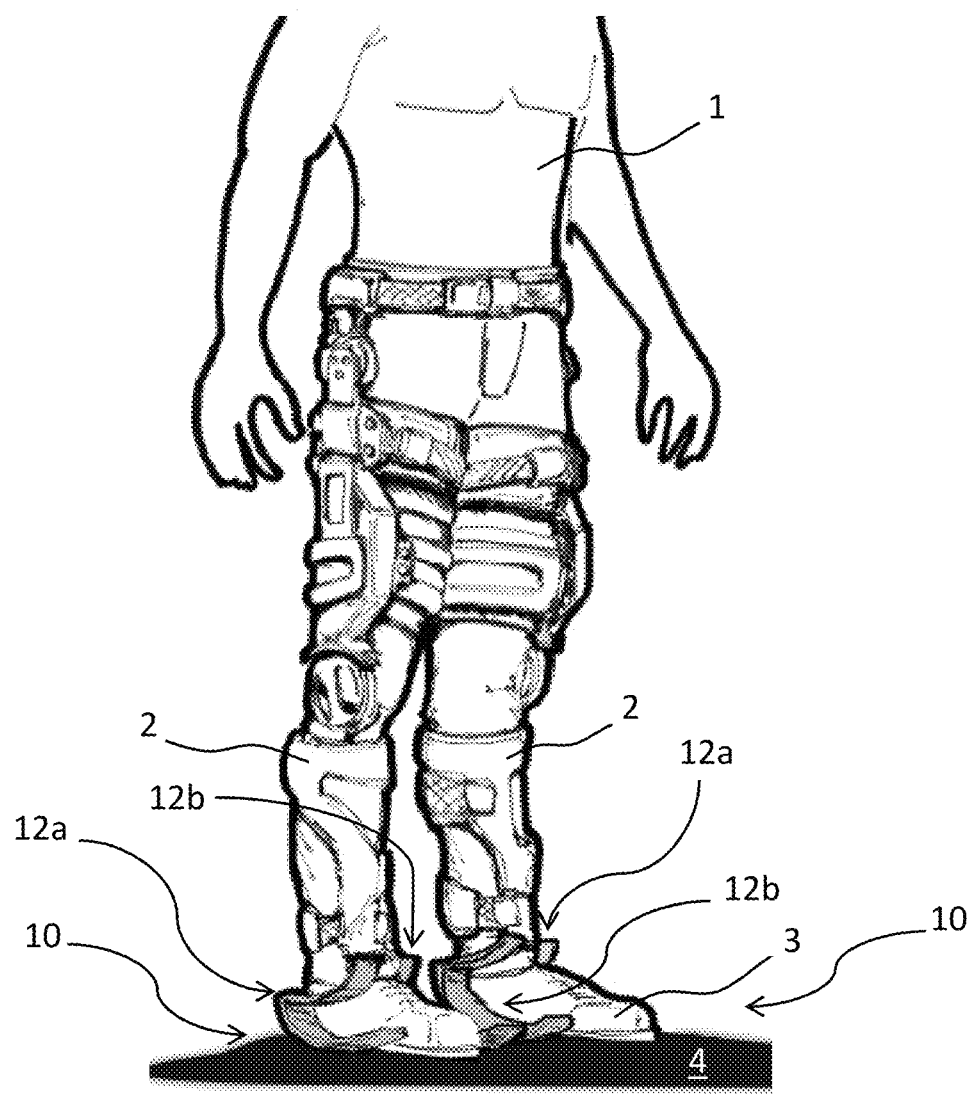
FIG. 1 is a front elevation perspective view of a user wearing lower extremity orthotic devices provided with load bearing assistance apparatuses in accordance with an illustrative embodiment of the present disclosure.

Referring to FIG. 1, there is shown a user 1 wearing lower extremity orthotic devices 2 provided with load bearing assistance apparatuses 10 in accordance with an illustrative embodiment of the present disclosure.

Figure 2:
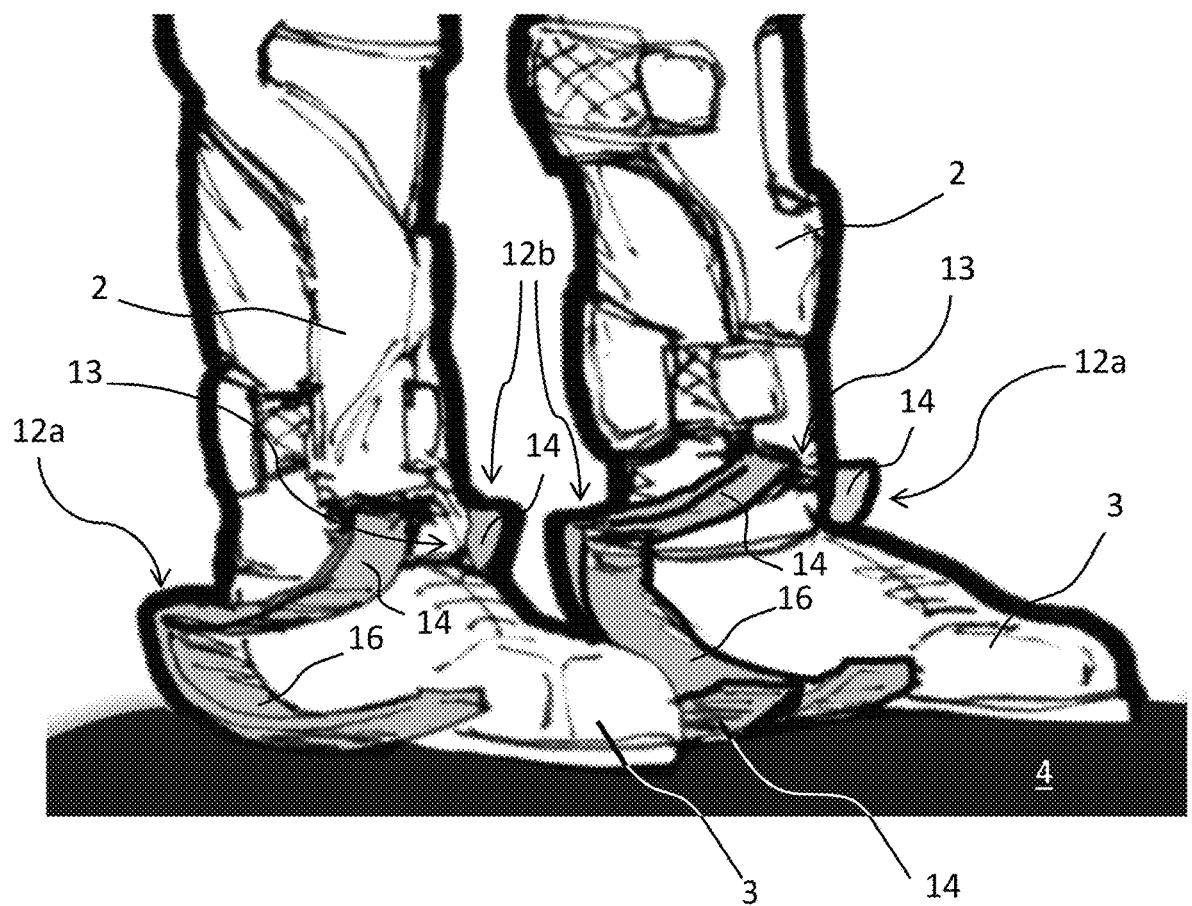
FIG. 2 is a front elevation perspective view of the load bearing assistance apparatuses of FIG. 1.
Figure 3:
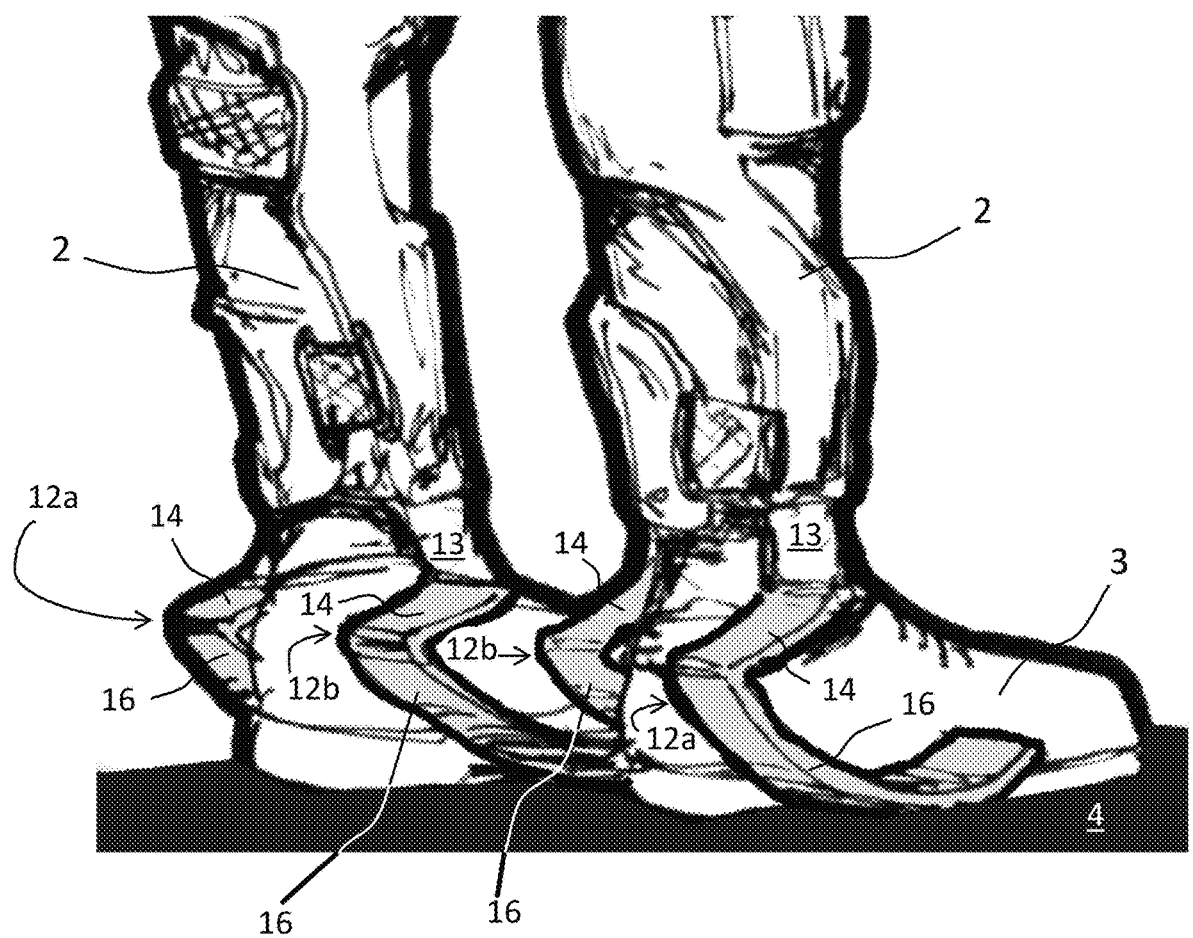
FIG. 3 is a back elevation perspective view of the load bearing assistance apparatuses of FIG. 1.

With further reference to FIGS. 2 and 3, the load bearing assistance apparatus 10 consist in a lateral 12a and a medial 12b spring-loaded members, each composed of a first 14 and second 16 convex elements connected at respective ends and a linking mechanism 13 for connecting the load bearing assistance apparatus 10 to a corresponding lower extremity orthotic device 2 and connecting the lateral 12a and medial 12b spring-loaded members in a spaced apart configuration so as to be positioned adjacent the lateral and medial portions, respectively, of the foot 3 of the user 1 of the lower extremity orthotic device 2 and such that the second 16 convex elements of the lateral 12a and medial 12b spring-loaded members are in contact with the ground 4.

The lateral 12a and medial 12b spring-loaded members provide, respectively, lateral and medial load transfer mechanical chains, which each partly absorb the weight of the associated orthotic device 2 and in some embodiments take over some of the dorsal load of the user as well. It is thus these four mechanical chains (one lateral and one medial mechanical chain for each of the left and right foot) that provide the load transfer capability from the lower extremity orthotic (or prosthetic) devices 2 to the ground 4.

Because of their positioning, the lateral 12a and medial 12b spring-loaded members transfer the load of the orthotic device 2 to the ground 4 regardless of the nature of the ground 4 (i.e. horizontal, stairs, uphill, downhill, etc.), while maintaining mobility (i.e. flexion/extension, inversion/eversion) of the foot 3, thus improving the user's 1 stability.

The shape of the second convex element 16 is optimized so as to be in contact with the ground 4 during all phases of locomotion (i.e. walking, running, etc.). Each spring-loaded member 12a, 12b is sufficiently robust so as to completely support the load of its associated orthotic device 2, for example when the user 1 is traveling over uneven terrain. In an alternative embodiment, the spring-loaded members 12a, 12b may be provided with a tension adjustment mechanism, for example a height adjustment mechanism, in order to adjust their load bearing capacity to suit various loads.

Figure 4:
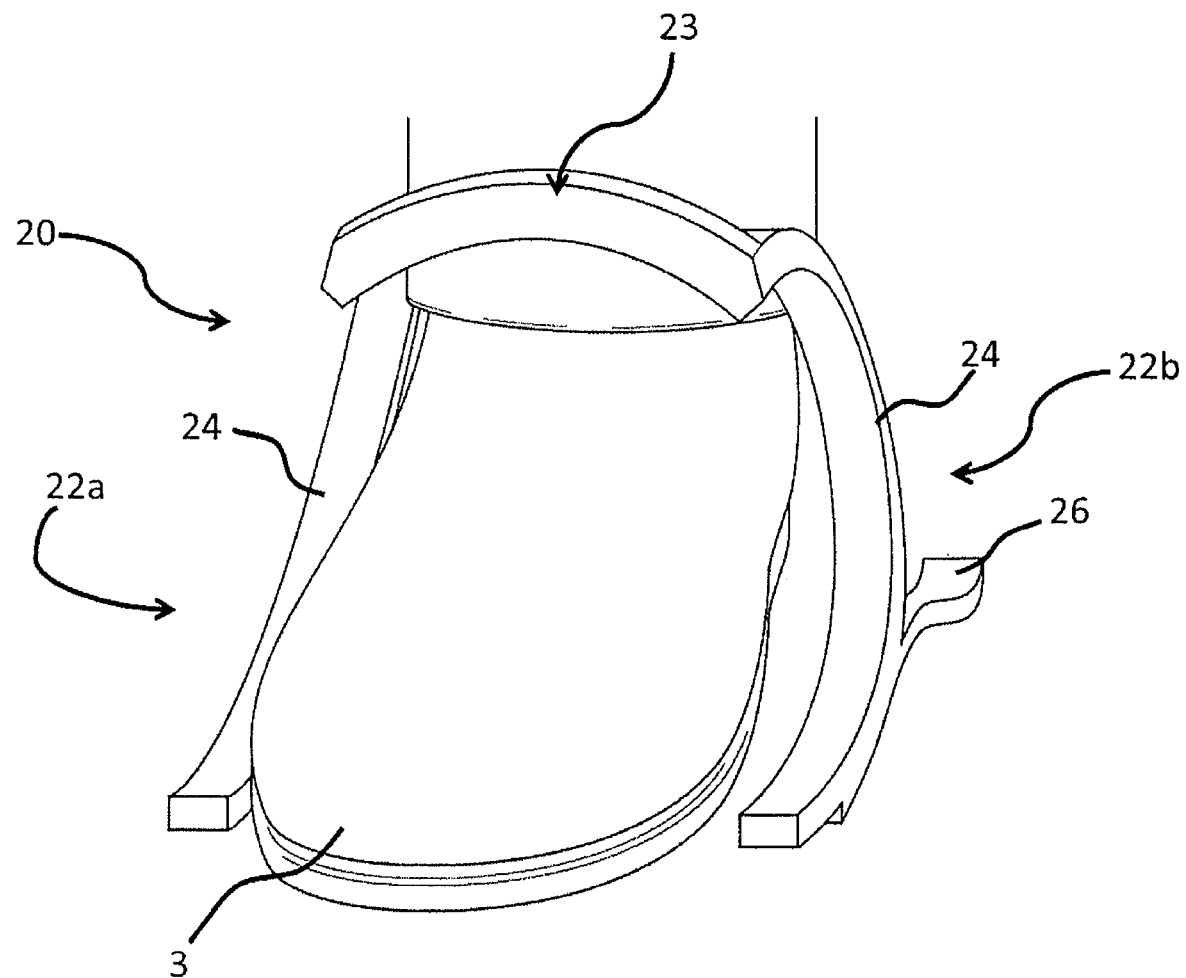
FIG. 4 is a front elevation perspective view of spring-loaded members in accordance with a first alternative embodiment of the present disclosure.

Referring now to FIG. 4, there is shown a lateral 22a and a medial 22b spring-loaded members in accordance with a first alternative embodiment. Each spring-loaded member 22a, 22b is composed of a side-wise C-like (U-like, cup-like, etc.) element 24 and a slightly downwardly curved longitudinal element 26.

Figure 5A:
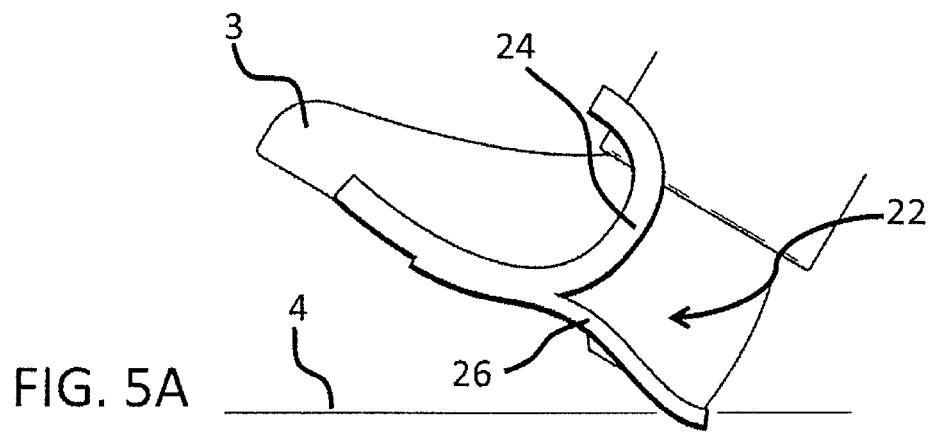
FIGS. 5A, 5B and 5C are schematic side views of the spring-loaded members of FIG. 4 showing ground contact during walking.
Figure 5B:
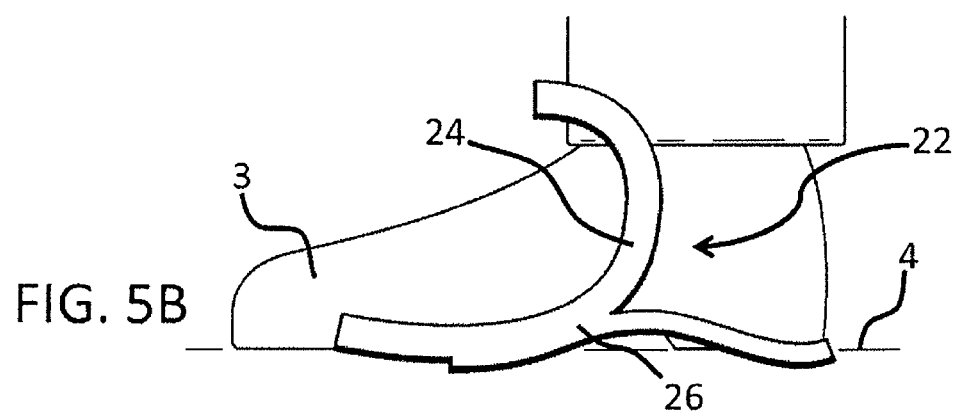
Figure 5C:
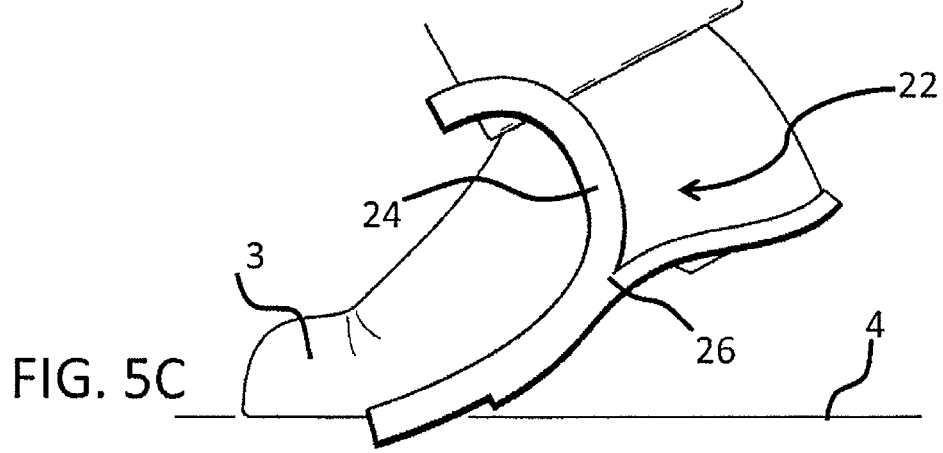

Referring to FIGS. 5A, 5B and 5C, there is shown contact of each of the spring-loaded members 22 with the ground 4 during locomotion. During heel strike a portion of the curved longitudinal element 26 is in contact with the ground 4, then during forefoot contact portions of both the C-like 24 and curved longitudinal 26 elements are in contact with the ground 4 and finally, during heel lift/forefoot loading a portion of the C-like 24 element is in contact with the ground 4.

Figure 6:
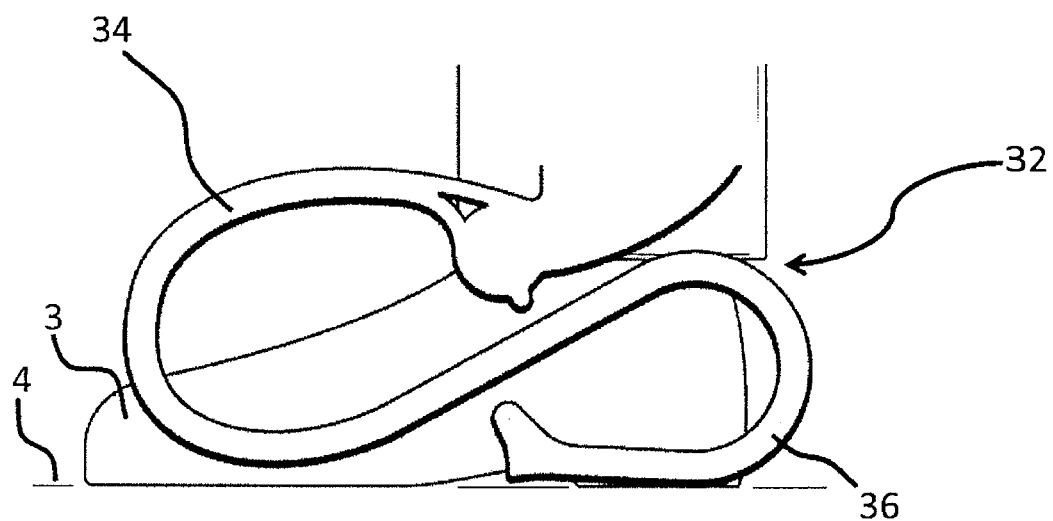
FIG. 6 is a schematic side view of a spring-loaded member in accordance with a second alternative embodiment of the present disclosure.

Referring to FIG. 6, there is shown a spring-loaded member 32 in accordance with a second alternative embodiment of the present disclosure. The spring-loaded member 32 is composed of two opposed side-wise C-like (U-like, cup-like, etc.) elements 34, 36 connected so as to form a generally S-like (serpentine-like, etc.) shape such that portions of either or both of the C-like elements 34, 36 are in contact with the ground 4 during locomotion.

It is to be understood that the shape (i.e. curvature, deformation, etc.) of the opposed side-wise C-like elements 34 and/or 36 may vary. For example, referring to FIG. 7, there is shown a spring-loaded member 42 in accordance with a third alternative embodiment of the present disclosure, composed of two the opposed side-wise C-like (U-like, cup-like, etc.) elements 44, 46 connected so as to form a generally compressed S-like (serpentine-like, etc.).

Figure 7:
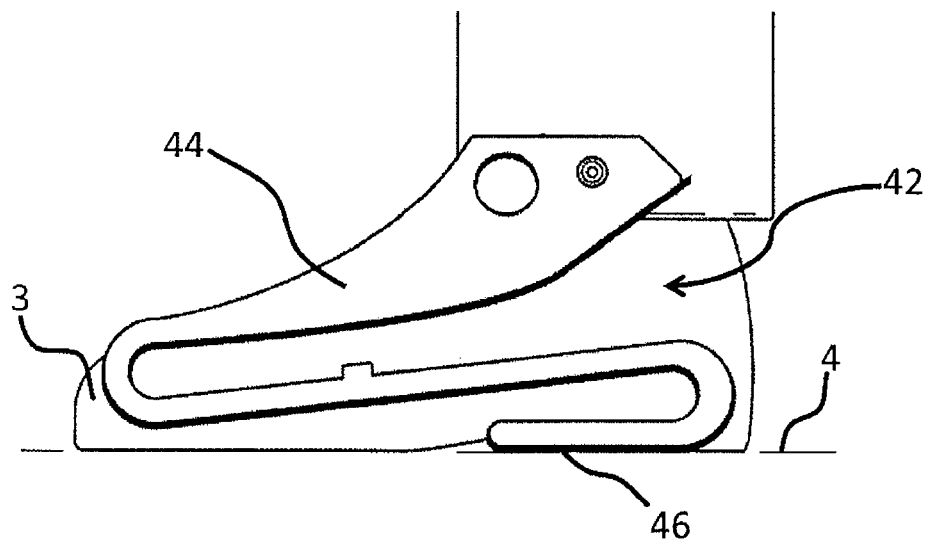
FIG. 7 is a schematic side view of a spring-loaded member in accordance with a third alternative embodiment of the present disclosure.

It is to be understood that in FIGS. 6 and 7 only one of the two spring-loaded members 32, 42 is shown as the lateral and medial spring-loaded members are similar in configuration.

It is further to be understood that depending on the exact configuration of the spring-loaded member 12, 22, 32, 42, one or more portions of either or both of the elements (14, 16), (24, 26), (34, 36), (44, 46) may be in contact with the ground 4 during locomotion.

Although the present disclosure has been described by way of particular non-limiting illustrative embodiments and examples thereof, it should be noted that it will be apparent to persons skilled in the art that modifications may be applied to the present particular embodiment without departing from the scope of the present disclosure as hereinafter claimed.

We claim:

1. A load bearing assistance apparatus for transferring load from a lower extremity orthotic or prosthetic device to the ground, comprising:
   a lateral and a medial spring-loaded members each having a top portion and a bottom portion linked by a curved portion, the top portion, the bottom portion and the curved portion forming an open shape with a cavity therein opened in a direction forward of the foot of the user, wherein each of the lateral and medial spring-loaded members is configured as a one-piece plate spring structure, wherein each of the lateral and medial spring-loaded members is configured to extend from a heel of the user and pass at least a middle portion of the foot of the user along a length of the foot of the user, the lateral and the medial spring-loaded members being configured to be positioned adjacent a lateral and a medial portions, respectively, of a foot of a user, wherein the lower extremity orthotic or prosthetic device is configured to be positioned above the foot of the user when in use, the top portions for securing to the lower extremity orthotic or prosthetic device and such that a convex surface of the bottom portion of each of the lateral and medial spring-loaded members enters in contact with the ground during locomotion;
   wherein in use the top portion, the bottom portion and the curved portion provide a spring-loaded effect transferring the load from the lower extremity orthotic or prosthetic device to the ground.

2. The load bearing assistance apparatus of claim 1, wherein the top portion, the bottom portion and the curved portion form superimposed first and second convex elements connected at respective ends.

3. The load bearing assistance apparatus of claim 1, wherein each of the lateral and medial spring-loaded members is composed of a side-wise C-shaped portion opened in a direction forward of the foot of the user and a curved longitudinal portion connected to a bottom portion of the C-shaped portion and extending in a direction backward of the foot of the user.

4. The load bearing assistance apparatus of claim 1, wherein each of the lateral and medial spring-loaded members is composed of two opposed side-wise top and bottom C-shaped portions connected on top one another as to form a S-shape with the top C-shaped portion opened in a direction backward of the foot of the user and the bottom C-shaped portion opened in a direction forward of the foot of the user.

\* \* \* \* \*